United States Patent
Kramer et al.

[11] 3,952,002
[45] Apr. 20, 1976

[54] TRIAZOLYL-O,N-ACETALS

[75] Inventors: Wolfgang Kramer; Karl Heinz Buchel; Werner Meiser, all of Wuppertal; Helmut Kaspers; Paul-Ernst Frohberger, both of Leverkusen, all of Germany

[73] Assignee: Bayer Aktiengesellschaft, Leverkusen, Germany

[22] Filed: Apr. 30, 1974

[21] Appl. No.: 465,713

[30] Foreign Application Priority Data
May 12, 1973 Germany............................ 2324010

[52] U.S. Cl. ........................ 260/308 R; 260/308 A; 424/269
[51] Int. Cl.² ............... C07D 249/08; C07D 249/04
[58] Field of Search ..................... 260/308 R, 308 A

[56] References Cited
UNITED STATES PATENTS
3,755,349  8/1973  Timmler et al. ................ 260/308 R Primary Examiner—Richard J. Gallagher
Assistant Examiner—Mark L. Berch
Attorney, Agent, or Firm—Burgess, Dinklage & Sprung

[57] ABSTRACT

Triazolyl-O,N-acetals of the formula

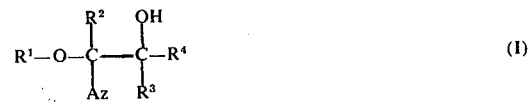

in which
$R^1$ and $R^4$ each independently is alkyl, alkenyl, alkynyl, cycloalkyl, cycloalkenyl, aryl, or aralkyl,
$R^2$ and $R^3$ each independently is hydrogen or one of the radicals mentioned under $R^1$, and
A is a 1,2,4-triazolyl-(1), 1,2,4-triazolyl-(4) or 1,2,3-triazolyl-(1)-radical,
which possess fungicidal and microbiostatic properties.

7 Claims, No Drawings

TRIAZOLYL-O,N-ACETALS

The present invention relates to and has for its objects the provision of particular new triazolyl-O,N-acetals, i.e. 1-organo-oxy-1-(1,2,4-triazolyl)-2-hydroxy-2-substituted-ethanol-2, which possess insecticidal or acaricidal properties, active compositions in the form of mixtures of such compounds with solid and liquid dispersible carrier vehicles, and methods for producing such compounds and for using such compounds in a new way especially for combating pests, e.g. fungi and microbes, with other and further objects becoming apparent from a study of the within specification and accompanying examples.

It has been disclosed in U.S. Pat. No. 3,321,366 and Belgian patent specification No. 738,095 that trityl-imidazoles and —1,2,4-triazoles, such as triphenylimidazole (Compound A) and triphenyl-1,2,4-triazole (Compound B), possess good fungicidal activity. However, their action is not always entirely satisfactory, especially if low amounts and concentrations are used. It is also known that zinc ethylene-1,2-bis-dithiocarbamate (Compound C) displays a good fungicidal activity against Phycomycetes, for example against *Phytophthora infestans*, the pathogen of potato blight and tomato blight, and against various soil-borne fungi. However, its activity if used as a seed dressing is not always entirely satisfactory.

The present invention provides, as new compounds, the triazolyl-O,N-acetals of the general formula

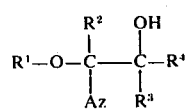  (I)

in which
$R^1$ and $R^4$ each independently is alkyl, alkenyl, alkynyl, cycloalkyl, cycloalkenyl, aryl, or aralkyl,
$R^2$ and $R^3$ each independently is hydrogen or one of the radicals mentioned under $R^1$, and
A is a 1,2,4-triazolyl-(1), 1,2,4-triazolyl-(4) or 1,2,3-triazolyl-(1) radical,
and their salts.

Surprisingly, the active compounds according to the invention display a substantially greater fungicidal action than the compounds triphenylimidazole, triphenyl-1,2,4-triazole and zinc ethylene-1,2-bis-dithiocarbamate known from the state of the art. The active compounds according to the invention thus represent an enrichment of the art.

Preferably $R^1$ is straight-chain or branched alkyl with 1 to 8 especially 1 to 4, carbon atoms, straight-chain or branched alkenyl with 2 to 6, especially 3 to 6, carbon atoms, straight-chain or branched alkynyl with 2 to 6, especially 3 to 6, carbon atoms, cycloalkyl or cycloalkenyl with in either cases 5 to 7, especially 5 or 6, carbon atoms, optionally substituted aryl with 6 to 10 carbon atoms or optionally substituted aralkyl with 6 to 10 carbon atoms in the aryl part and 1 or 2 carbon atoms in the alkyl part, the preferred substituents being selected from halogen, especially fluorine, chlorine or bromine, straight-chain or branched alkyl with 1 to 6, especially 1 to 4, carbon atoms, alkoxy with 1 to 4, especially 1 or 2, carbon atoms, halogenoalkyl with 1 or 2 carbon atoms and 1 to 5 halogen atoms, especially fluorine and chlorine, halogenoalkylthio with 1 or 2 carbon atoms and 3 to 5 halogen atoms, especially fluorine and chlorine, for example chlorodifluoromethylthio, carbalkoxy with 1 to 4 carbon atoms in the alkoxy part, phenyl in the o- or p-position, and nitro;

$R^2$ is hydrogen, straight-chain or branched alkyl with 1 to 6, especially 1 to 4, carbon atoms, straight-chain or branched alkenyl with 2 to 6, especially 2 to 4 carbon atoms, straight-chain or branched alkynyl with 2 to 6, especially 3 to 5, carbon atoms, cycloalkyl or cycloalkenyl with in either cases 5 to 7, especially 5 or 6, carbon atoms, optionally substituted aryl with 6 to 10 carbon atoms or optionally substituted aralkyl with 6 to 10 carbon atoms in the aryl part and 1 or 2 carbon atoms in the alkyl part, the preferred substituents being selected from halogen, especially fluorine, chlorine or bromine, straight-chain or branched alkyl with 1 to 4 carbon atoms and halogenoalkyl with 1 or 2 carbon atoms and 2 to 5 halogen atoms, especially fluorine or chlorine;

$R^3$ is hydrogen, alkyl, alkenyl or alkynyl with in each case up to 8, especially with up to 4, carbon atoms, cycloalkyl with 5 or 6 carbon atoms, especially cyclohexyl, aryl with 6 to 10 carbon atoms or optionally substituted aralkyl with 6 to 10 carbon atoms in the aryl part and 1 or 2 carbon atoms in the alkyl part, the preferred substituents being selected from fluorine, chlorine, and alkyl and alkoxy with in either case up to 4 carbon atoms; and Az is one of the following radicals:

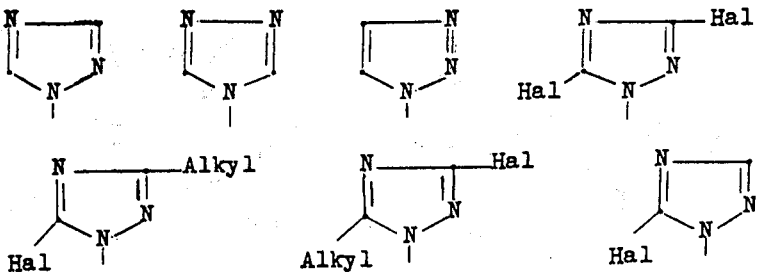

wherein Hal is halogen, especially chlorine or bromine, and 'Alkyl' is preferably $CH_3$.

The compounds of the formula (I) possess two asymmetrical carbon atoms and can therefore be in the erythro form and in the threo form; in both cases they are predominantly in the form of racemates.

The present invention also provies a process for the preparation of a compound of the general formula (I) in which a triazole derivative of the general formula

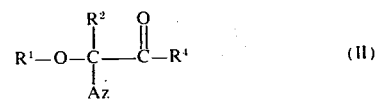  (II)

in which

R¹, R², R⁴ and Az have the above-mentioned meanings, is a. reduced with hydrogen in the presence of a catalyst and optionally of a polar solvent, or b. reduced with aluminum isopropylate in the presence of a solvent, or c. reduced with complex hydrides, optionally in the presence of a polar solvent, or d. reduced with formamidine-sulfinic acid and alkali metal hydroxide, optionally in the presence of a polar solvent, or e. reacted with an organo-metallic compound of the general formula

$$M - R^3 \qquad (III),$$

in which

R³ has the above-mentioned meaning, and

M is an alkali metal or the radical X—Mg, wherein X is chlorine, bromine or iodine, in the presence of an inert solvent.

If 1-phenoxy-1-[1,2,4-triazolyl-(1')]-3,3-dimethyl-butan-2-one and hydrogen are used as starting materials, the course of the reaction in process variant (a) can be represented by the following equation:

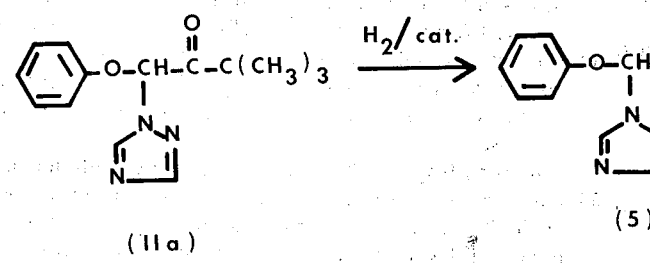

If 1-phenoxy-1-[1,2,4-triazolyl-(1')]-3,3-dimethyl-butan-2-one and aluminum isopropylate are used as starting materials, the course of the reaction in process variant (b) can be represented by the following equation:

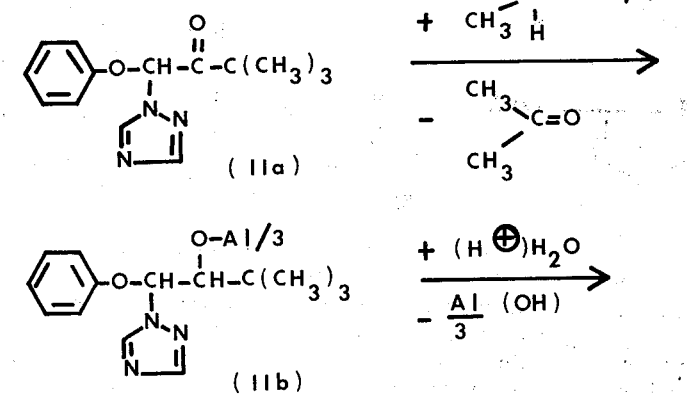

If 1-phenoxy-1-[1,2,4-triazolyl-(1')]-3,3-dimethyl-butan-2-one and sodium borohydride are used as starting materials, the course of the reaction in process variant (c) can be represented by the following equation:

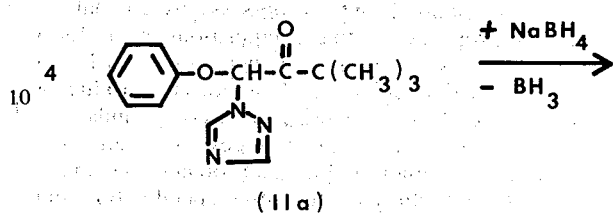

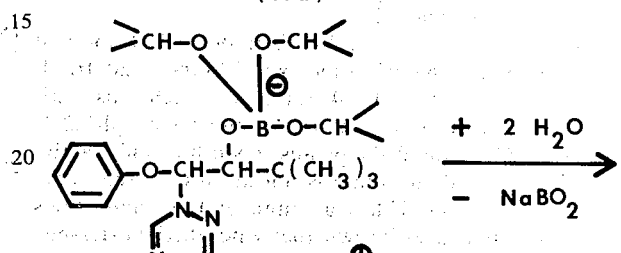

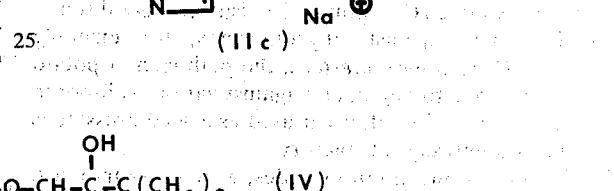

If 1-phenoxy-1-[1,2,4-triazolyl-(1')]-3,3-dimethyl-butan-2-one and formamidinesulfinic acid are used as starting materials, the course of the reaction in process variant (d) can be represented by the following equation:

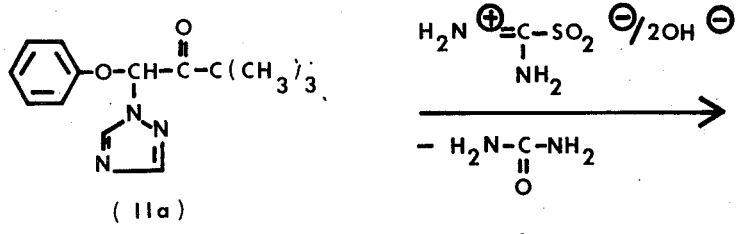

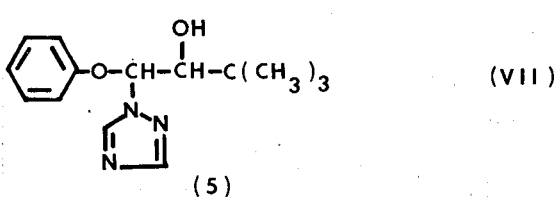

If 1-phenoxy-1-[1,2,4-triazolyl-(1')]-3,3-dimethyl-butan-2-one and methyl-magnesium iodide are used as starting materials, the course of the reaction in process variant (e) can be represented by the following equation:

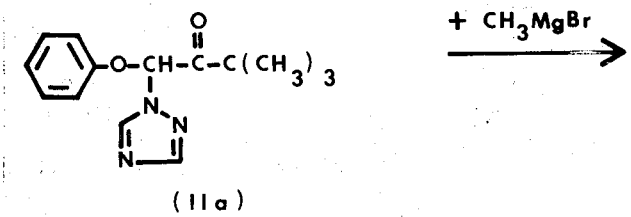

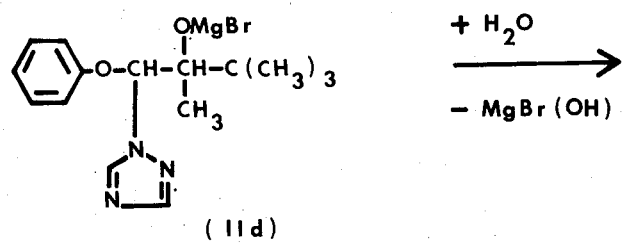

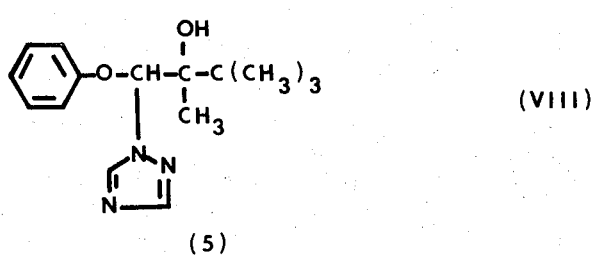

The following may be mentioned as examples of starting compounds of the formula (II): [ω-(1,2,4-triazolyl-1')]-[ω-phenoxy]-acetophenone; [ω-(1,2,4-triazolyl-1')]-[ω-4'-chlorophenoxy]-acetophenone; [ω-(1,2,4-triazolyl-1')]-[ω-3'-chlorophenoxy]-acetophenone; [ω-(1,2,4-triazolyl-1')]-[ω-2',4'-dichlorophenoxy]-acetophenone; [ω-(1,2,4-triazolyl-1')]-[ω-2',4'-dichlorophenoxy]-4-chloro-acetophenone; [ω-(1,2,4-triazolyl-1')]-[ω-2',6'-dichlorophenoxy]-acetophenone; [ω-(1,2,4-triazolyl-1')]-[ω-4'-methoxyphenoxy]-acetophenone; [ω-(1,2,4-triazolyl-1')]-[ω-4'-methylphenoxy]-acetophenone; [ω-(1,2,4-triazolyl-1')]-[ω-2'-methylphenoxy]-acetophenone; [ω-methyl]-[ω-(1,2,4-triazolyl-1')]-[ω-4'-chlorophenoxy]-acetophenone; [ω-phenyl]-[ω-(1,2,4-triazolyl-1')]-[ω-2',4'-dichlorophenoxy]-acetophenone; [ω-phenyl]-[ω-(1,2,4-triazolyl-1')]-[ω-2',5'-dichlorophenoxy]-acetophenone; [2-(1,2,4-triazolyl-1')]-[2-(2',4'-dichlorophenoxy]-acetaldehyde; [1-(1,2,4-triazolyl-1')]-[1-(2',4'-dichlorophenoxy]-propan-2-one; [2-(1,2,4-triazolyl-1')]-[2-phenoxy]-butan-3-one; [2-(1,2,4-triazolyl-1')]-[2-(4'-chlorophenoxy)]-butan-3-one; [2-(1,2,4-triazolyl-1')]-[4'-fluorophenoxy)]-butan-3-one; [2-(1,2,4-triazolyl-1')]-[2-(2',4'-dichlorophenoxy)]-butan-3-one; [1-(1,2,4-triazolyl-1')]-[1-(2',4'-dichlorophenoxy)]-3-methyl-butan-2-one; [2-(1,2,4-triazolyl-1')]-[2-(4'-chlorophenoxy)]-4-methyl-pentan-3-one; [2-(1,2,4-triazolyl-1')]-[2-(2',4'-dichlorophenoxy)]-4-methyl-pentan-3-one; [1-(1,2,4-triazolyl-1')]-[1-(4'-chlorophenoxy)]-3,3-dimethyl-butan-2-one; [1-(1,2,4-triazolyl-1')]-[1-(2',4'-dichlorophenoxy)]-3,3-dimethyl-butan-2-one; [1-(1,2,4-triazolyl-1')]-[1-(2',5'-dichlorophenoxy)]-3,3-dimethyl-butan-2-one; [1-(1,2,4-triazolyl-1')]-[1-(2',6'-dichlorophenoxy)]-3,3-dimethyl-butan-2-one; [1-(1,2,4-triazolyl-1')]-[1-(2',4',6'-trichlorophenoxy)]-3,3-dimethyl-butan-2-one; [1-(1,2,4-triazolyl-1')]-[1-(2'-chlorophenoxy)]-3,3-dimethyl-butan-2-one; [1-(1,2,4-triazolyl-1')]-[1-(4'-bromophenoxy)]-3,3-dimethyl-butan-2-one; [1-(1,2,4-triazolyl-1')]-[1-(4'-fluorophenoxy)]-3,3-dimethyl-butan-2-one; [1-(1,2,4-triazolyl-1')]-[1-(4'-methylphenoxy)]-3,3-dimethyl-butan-2-one; [1-(1,2,4-triazolyl-1')]-[1-(4'-methoxyphenoxy)]-3,3-dimethyl-butan-2-one; [1 -(1,2,4-triazolyl-1')]-[1-(4'-tert.-butylphenoxy)]-3,3-dimethyl-butan-2-one; [1-(1,2,4-triazolyl-1')]-[1-(4'-isopropylphenoxy)]-3,3-dimethyl-butan-2-one; [1-(1,2,4-triazolyl-1')]-[1-(2'methyl-4'-chlorophenoxy)]-3,3-dimethyl-butan-2-one; [1-(1,2,4-triazolyl-1')]-[1-(4'-trifluoromethylphenoxy)]-3,3-dimethyl-butan-2-one; [1-(1,2,4 -triazolyl-1')]-[1-(4'-nitrophenoxy)]-3,3-dimethyl-butan-2-one; [1-(1,2,4-triazolyl-1')]-[1-(2'-nitrophenoxy)]-3,3-dimethyl-butan-2-one; [1-(1,2,4-triazolyl-1')]-[1-(4'-fluorodichloromethylmercaptophenoxy)]-3,3-dimethyl-butan-2-one; [1-(1,2,4-triazolyl-1')]-[1-(p-diphenoxy)]-3,3-dimethyl-butan-2-one; [1-(1,2,4-triazolyl-1')]-[1-(o-diphenoxy)]-3,3-dimethyl-butan-2-one; [2-(1,2,4-triazolyl-1')]-[2-phenoxy]-4,4-dimethyl-pentan-3-one; [2-(1,2,4-triazolyl-1')]-[2-(4-fluorophenoxy)]-4,4-dimethyl-pentan-3-one; [2-(1,2,4-triazolyl-1')]-[2-(2',4'-dichlorophenoxy)]-4,4-dimethyl-pentan-3-one; [1-phenyl]-[1-(1,2.4-triazolyl-1')]-[1-phenoxy]-3,3-dimethyl-butan-2-one; [1-phenyl]-[1-(1,2,4-triazolyl-1')-[1-(4'-fluorophenoxy)]-3,3-dimethyl-butan- 2-one; [1-phenyl]-[1-(1,2,4-triazolyl-1')]-[1-(2',4'-dichlorophenoxy)]-3,3-dimethyl-butan-2-one; [2-(1,2,4-triazolyl-1')]-[2-(2',-4'-dichlorophenoxy)]-1-cyclohexyl-ethan-1-one; [2-(1,2,4-triazolyl-1')]-[2-(2',4'-dichloro-phenoxy)]-1-cyclopentyl-ethan-1-one and [2-(1,2,4-triazolyl-1')]-[2-(2',4'-dichlorophenoxy)]-3 cyclohexyl-propan-3-one.

The triazole derivatives of the formula (II) which can be used according to the invention have not previously been described in the literature but they form, in part, the subject matter of application Ser. No. 318,963, filed Dec. 27, 1972, now U.S. Pat. No. 3,912,752. They can be prepared, for example, by reacting a halogenoether-ketone with a 1,2,4-triazole in a stoichiometric ratio, optionally in the presence of a solvent or diluent and of an acid-binding agent, at temperatures of, preferably, 80° to 120°C. Amongst other processes of preparation, the reaction of hydroxyether-ketones with 1,2,4-triazoles in the presence of a dehydrating agent and optionally in the presence of a diluent, at temperatures between, preably, 140° and 200°C, should also be mentioned.

Depending on the process of preparation and on the conditions of working up, the triazole derivatives of the formula (II) may be obtained as 1,2,4-triazolyl-(4) derivatives or as 1,2,4-triazolyl-(1) derivatives in accordance with the tautomeric character of 1,2,4-triazole

;

a mixture of both forms frequently results.

Salts of compounds of the formula (I) which can be used are salts with physiologically tolerated acids. Preferred acids include the hydrogen halide acids, such as hydrobromic acid and, in particular, hydrochloric acid, as well as phosphoric acid, monofunctional and bifunctional aliphatic or aromatic carboxylic acids and hydroxycarboxylic acids, such as acetic acid, maleic acid, succinic acid, fumaric acid, tartaric acid, citric acid, salicylic acid, sorbic acid and lactic acid, and 1,5-naphthalene-disulfonic acid.

Polar organic solvents can be used as diluents for the reaction in accordance with process variant (a). Preferred solvents include alchohols, such as methanol and ethanol, and nitriles, such as acetonitrile. The reaction is carried out in the presence of a catalyst. Preferably, noble metal catalysts, noble metal oxide (or noble metal hydroxide) catalysts or Raney catalysts are used, especially platinum, platinum oxide or nickel. The reaction temperatures can be varied within a fairly wide range: in general, the reaction is carried out at from 20° to 50°C, preferably at from 20° to 40°C. The reaction can be carried out under normal pressure and under elevated pressure (1 to 2 atmospheres gauge). In the reaction according to variant (a), about 1 mole of hydrogen and 0.1 mole of catalyst are generally employed per 1 mole of the compound of the formula (II); to isolate the compound, the catalyst is filtered off, the filtrate is freed from the solvent in vacuo and the resulting product of the formula (I) is purified by recrystallization. If desired, the salts of the compounds according to the invention are obtained according to customary methods.

If process variant (b) is followed, preferred diluents for the reaction are alcohols, such as isopropanol, or inert hydrocarbons, such as benzene. The reaction temperatures can again be varied within a fairly wide range; in general, the reaction is carried out at from 20° to 120°C, preferably at 50° to 100°C. About 1 to 2 moles of aluminum isopropylate are generally employed per mole of the compound of the formula (II) in carrying out the reaction. To isolate the compound of the formula (I), the excess solvent is removed by distillation in vacuo and the resulting aluminum compound is decomposed with dilute sulfuric acid or sodium hydroxide solution. The further working-up is carried out in the customary manner.

If process variant (c) is followed, possible diluents for the reaction are polar organic solvents, preferably alcohols, such as methanol, ethanol, butanol and isopropanol, and ethers, such as diethyl ether or tetrahydrofuran. In general, the reaction is carried out at from 0° to 30°C, preferably at from 0° to 20°C. For this reaction, about 1 mole of a complex hydride, such as sodium borohydride or lithium alanate, is generally employed per mole of the compound of the formula (II). To isolate the compound of the formula (I), the residue is taken up in dilute hydrochloric acid and the solution is then rendered alkaline and extracted with an organic solvent. The further working-up is carried out in the usual manner.

Possible diluents for the reaction according to process variant (d) are polar organic solvents, preferably alcohols, such as methanol and ethanol, as well as water. Here again the reaction temperatures can be varied within a fairly wide range; in general, the reaction is carried out at a temperature of from 20° to 100°C, preferably at from 50° to 100°C. To carry out the reaction, about 1 to 3 moles of formamidinesulfinic acid and 2 to 3 moles of alkali metal hydroxide are generally employed per mole of the compound of the formula (II). To isolate the end product, the reaction mixture is freed from the solvent and the residue is extracted with water and organic solvents, and worked up and purified in the customary manner; if desired, the salt is prepared.

In the reaction according to process variant (e), compounds of the general formula (I) in which $R^3$ is not hydrogen are obtained. In contrast thereto, the reactions according to process variants (a) to (d) are reduction reactions; the compounds of the formula (I) thereby obtained are secondary alcohols in which $R^3$ is, in every case, hydrogen only.

For the reaction according to process variant (e), an organo-metallic compound of the formula (III) is required in addition to the triazole derivative of the formula (II). M in the formula (III) is preferably lithium, sodium or a so-called "Grignard grouping" Mg—X, wherein X is chlorine, bromine or iodine. The organo-metallic compounds of the formula (III) are generally known: a summary and survey of numerous publications is to be found, for example, in G.E. Coates, "Organo-Metallic Compounds", 2nd edition, Methuen and Co, London (1960).

Anhydrous ethers, such as diethyl ether or dibutyl ether, are preferably used for the reaction in accordance with process variant (e). The reaction temperature can, in general, be from 0° to 80°C, preferably from 30° to 60°C. In carrying out the process variant (e), about 1 mole of the organo-metallic compound of the formula (III) is generally employed per mole of the compound of the formula (II). The mixtures obtained by organo-metallic reactions are worked up in the customary and generally known manner.

The active compounds according to the invention display a strong fungitoxic action. They do not harm crop plants in the concentrations required to combat fungi. For these reasons, they are suitable for use as plant-protection agents for combating fungi. Fungitoxic agents are employed in plant protection for combating Archimycetes, Phycomycetes, Ascomycetes, Basidiomycetes and *Fungi Imperfecti*.

The active compounds according to the invention have a very broad spectrum of action and can be employed against parasitory fungi which attack above-ground parts of plants or attack the plants through the soil, and against seed-transferble pathogens.

They display particularly good action against parasitory fungi on above-ground parts of plants, such as species of Erysiphe, species of Podosphaera, species of Sphaerotheca, species of Venturia and also species of Piricularia and species of Pellicularia. They are also highly active against rust fungi and smut fungi, for example against the pathogen of bunt of wheat. It is to be emphasized that the active compounds according to the invention display not only a protective action but also a curative action; that is to say, they can also be employed after infection has occurred. The systemic action of the compounds should also be pointed out. Thus it proves possible to protect plants against fungal attack by supplying the active compound to the above-ground part of plants through the soil, through the plant or through the seed. As plant protection agents, the compounds according to the invention can be used for the treatment of soil, for the treatment of seed and for the treatment of above-ground parts of plants.

The compounds according to the invention are well tolerated by plants. They only have a low toxicity to warm-blooded animals and because of their only slight odor and good tolerance are not unpleasant to the human skin when handled.

The active compounds according to the invention also display a good microbistatic activity.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and microbistats, or insecticides, acaricides, bactericides, rodenticides, nematocides, herbicides, fertilizers, plant nutrients, growthregulating agents, agents for improving the soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.00001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, the concentrations of active compound in the application forms can be varied within a fairly wide range. In general, the concentrations are between about 0.1 and 0.00001 per cent by weight, preferably between about 0.05 and 0.0001 per cent.

In the treatment of seed, the amounts of active compound required are, in general, from about 0.001 to 50 g per kilogram of seed, preferably about 0.01 to 10 g per kilogram.

The amounts of active compound required for soil treatment are generally from about 1 to 1,000 g per cubic meter of soil, preferably about 10 to 200 g.

Furthermore, the present invention contemplates methods of selectively killing, combating or controlling pests, e.g. fungi and microbes, and more particularly methods of combating fungi, which comprises applying to at least one of correspondingly (a) such fungi, (b) such microbes, and (c) the corresponding habitat thereof, i.e. the locus to be protected, a correspondingly combative or toxic amount, i.e. a fungicidally or microbistatically effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1 a. Preparation of the intermediate: ω-Bromo-ω-(4'-chlorophenoxy)-acetophenone, required as the starting material for the preparation of an intermediate, was prepared by condensation of 4-chlorophenol with ω-chloroacetophenone and bromination of the resulting ω-(4'-chlorophenoxy)-acetophenone in the usual manner, and had a melting point of 71°C.

32.5 g (0.1 mole) of ω-bromo-ω-(4'-chlorophenoxy)-acetophenone and 30 g (0.44 mole) of 1,2,4-triazole were dissolved in 240 ml of acetonitrile and the solution was heated for 48 hours under reflux. After distilling off the solvent, the residue was taken up in 800 ml of water. This aqueous solution was repeatedly extracted with methylene chloride and the methylene chloride solution was twice washed with 200 ml of water at a time and then dried over sodium sulfate, and the solvent was distilled off in vacuo. The residue crystallized out; it could be recrystallized from ligroin/isopropanol (2 : 1); the melting point was about 98° to 100°C.

b.

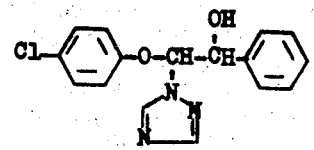

(1)

31.4 g of (0.1 mole) of ω-[4'-chlorophenoxy]-ω-[1,2,4-triazolyl-(1')]-acetophenone were dissolved in 300 ml of methanol and 3 g (0.08 mole) of sodium borohydride were introduced into this solution while stirring and cooling with ice. The reaction mixture was stirred for 1 hour at room temperature and the solvent was then distilled off in vacuo. The residue was taken up in dilute hydrochloric acid and the solution was briefly heated and filtered. The filtrate was then rendered alkaline with sodium hydroxide solution. The precipitate thereby produced was filtered off and taken up in ethyl acetate. After distilling off the ethyl acetate, an oil remained, which crystallized on trituration with ligroin. After recrystallization from ligroin/isopropanol, 25 g (98% of theory) of 1-(4'-chlorophenoxy)-1-[1,2,4,-triazolyl-(1')]-2-phenyl-ethanol-2 of melting point 117°C were obtained.

EXAMPLE 2

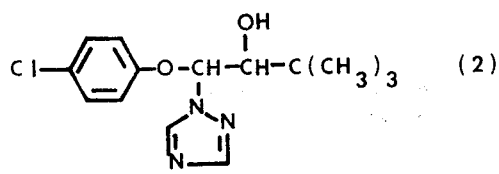

587 g (2 moles) of 1-(4'-chlorophenoxy)-1-[1,2,4-triazolyl-(1')]-3,3-dimethyl-butan-2-one were dissolved in 3 l of methanol. A total of 80 g (2 moles) of sodium borohydride was added thereto in portions of 5 g at 0° to 10°C, while stirring and cooling with ice, and the mixture was stirred for 2 hours at 5° to 10°C and then for 12 hours at room temperature. It was then cooled to 10°C and 300 g (3 moles) of concentrated aqueous hydrochloric acid were added at 10° to 20°C. After stirring for six hours at room temperature, the resulting suspension was diluted with 3.8 l of water which contained 400 g (4.8 moles) of sodium bicarbonate. The precipitate thereby produced was filtered off. 502 g (85% of theory) of 1-(4'-chlorophenoxy)-1-[1,2,4-triazolyl-(1')]-3,3-dimethyl-butan-2-ol of melting point 112° to 117°C were obtained.

EXAMPLE 3

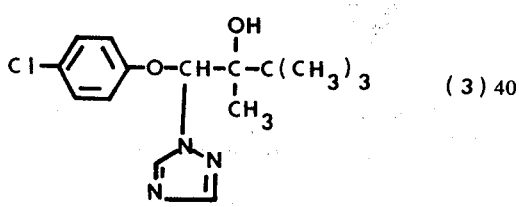

A solution of 31.2 g (0.22 mole) of methyl iodide in 100 ml of anhydrous ether was added dropwise to a suspension of 4.8 g (0.22 mole) of magnesium filings in 50 ml of anhydrous ether, with stirring and reflux cooling; during the addition, the solvent started to boil. After completion of the addition, a solution of 29.4 g (0.1 mole) of 1-(4'-chlorophenoxy)-1-[1,2,4-triazolyl-(1')]-3,3-dimethyl-butan-2-one in 100 ml of anhydrous ether was added dropwise to this "Grignard solution" and the mixture was heated to the boil for 18 hours with reflux cooling. After cooling, the reaction mixture was introduced into a solution of 80 g of ammonium chloride in 600 ml of water, 250 ml of ethyl acetate were added and the mixture was stirred for 15 minutes. The organic phase was separated off and the aqueous phase was extracted with ethyl acetate. Both ethyl acetate extracts were washed twice with 100 ml of water at a time, dried over sodium sulfate and freed of the solvent in vacuo. The crystalline precipitate was taken up in hot petroleum ether, in which it remained undissolved, and was filtered off hot. 11 g (36% of theory) of 1-(4'-chlorophenoxy)-1-[1,2,4-triazolyl-(1')]-2,3,3-trimethyl-butan-ol of melting point 158° to 160°C were obtained.

EXAMPLE 4

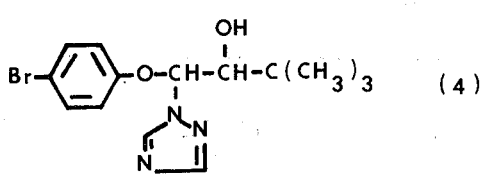

33.6 g (0.1 mole) of 1-(4'-bromophenoxy)-1-[1,2,4-triazolyl-(1')-]-3,3-dimethyl-butan-2-one were dissolved in 300 ml of ethanol and a sodium hydroxide solution, containing 8 g (0.2 mole) of sodium hydroxide in 40 ml of water, was added thereto, followed by 32.4 g (0.3 mole) of formamidinesulfinic acid. The reaction mixture was heated to the boil under reflux for 3 hours and filtered, and the solvent was distilled in vacuo. The oily residue was taken up in 100 ml of water and extracted twice with 100 ml of methylene chloride. The combined organic phases were washed twice with 100 ml of water, dried over sodium sulfate and freed of the solvent in vacuo. The resulting oil was boiled up with petroleum ether, whereupon it crystallized. Filtration gave 26.5 g (79% of theory) of 1-(4'-bromophenoxy)-1-[1,2,4-triazolyl-(1')]-3,3-dimethyl-butan-2-ol of melting point 115° to 118°C.

EXAMPLE 5

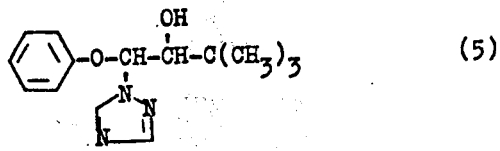

(erythro form and threo form)

29.5 g (0.114 mole) of 1-phenoxy-1-[1,2,4,-triazolyl-(1')]-3,3-dimethyl-butan-2-one were dissolved in 250 ml of methanol and 5.8 g (0.15 mole) of sodium borohydride were added in portions at 0° to 5°C, with stirring and reflux cooling. After stirring for twelve hours at room temperature the mixture was next worked up, as described in Example 2, with 20 ml of concentrated hydrochloric acid and 250 ml of saturated sodium bicarbonate solution. The suspension containing sodium bicarbonate was extracted twice with 150 ml of methylene chloride at a time. The combined organic extracts were washed twice with 100 ml of water until neutral, dried and freed of the solvent in vacuo. The resulting oil was boiled up with hot petroleum ether. This left a crystalline residue (A) which was filtered off hot, and dried. The filtrate was freed of the solvent in vacuo and this residue (B) was triturated with petroleum ether and a little ether. A total of 23.4 g (79% of theory) of 1-phenoxy-1-[1,2,4-triazolyl-(1')]-3,3-dimethyl-butan-2-ol is obtained, comprising 4.1 g (residue A) of the erythro-form of melting point 132°C and 19.3 g (residue B) of the threo-form of melting point 88° to 94°C.

The following compounds of the formula

were obtained analogously:

Table 1
| Compound No. | R¹ | R² | R³ | R⁴ | Az | Melting point (°C) or refractive index ($n_D^{20}$) |
|---|---|---|---|---|---|---|
| 6 | 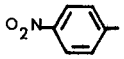 | H | H | C(CH₃)₃ |  | 194 – 196 |
| 7 | 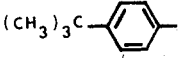 | H | H | C(CH₃)₃ |  | 113 – 117 |
| 8 | 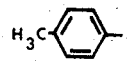 | H | H | C(CH₃)₃ |  | 123 – 127 |
| 9 |  | H | H | C(CH₃)₃ |  | 107 – 112 |
| 10 |  | H | H | C(CH₃)₃ |  | 114 – 115 |
| 11 |  | H | H | C(CH₃)₃ |  | 99 – 110 |
| 12 | 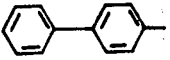 | H | H | C(CH₃)₃ |  | 98 – 100 |
| 13 |  | H | H | C(CH₃)₃ |  | threo: 115 – 117<br>erythro: 186 – 190 |
| 14 | 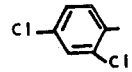 | H | H | C(CH₃)₃ |  | threo: 114 – 116<br>erythro: 161 – 164 |
| 15 | 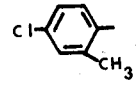 | H | H | C(CH₃)₃ |  | 107 – 110 |
| 16 | 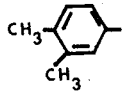 | H | H | C(CH₃)₃ |  | 133 – 135 |
| 17 | 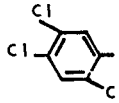 | H | H | C(CH₃)₃ |  | 137 – 144 |

Table 1-continued

| Compound No. | R¹ | R² | R³ | R⁴ | Az | Melting point (°C) or refractive index ($n_D^{20}$) |
|---|---|---|---|---|---|---|
| 18 | 2,4-Cl₂-C₆H₃– | H | H | C(CH₃)₃ | 1,2,4-triazol-1-yl | 185 – 187 |
| 19 | 4-Cl-C₆H₄– | H | H | CH₃ | 1,2,4-triazol-1-yl | 84 – 90 |
| 20 | 2,4-Cl₂-C₆H₃– | H | CH₃ | C(CH₃)₃ | 1,2,4-triazol-1-yl | 101 – 103 |
| 21 | 4-Cl-C₆H₄– | H | –CH₂–C₆H₅ | C(CH₃)₃ | 1,2,4-triazol-1-yl | 113 – 116 |
| 22 | 4-(CH₃O-CO)-C₆H₄– | H | H | C(CH₃)₃ | | 136 – 138 |
| 23 | 2-Cl-biphenyl– | H | H | C(CH₃)₃ | | 95 – 98 |
| 24 | 3,5-Cl₂-biphenyl– | H | H | C(CH₃)₃ | | 142 – 144 |

EXAMPLE 6

Erysiphe test / protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23°–24°C and at a relative atmospheric humidity of about 75%.

After 12 days, the infection of the cucumber plants was determined as a percentage of the untreated but also inoculated control plants. 0% means no infection; 100% that the infection was exactly as great as in the case of the control plants.

The active compounds, the concentrations of the active compounds and the results can be seen from the following table:

Table 2

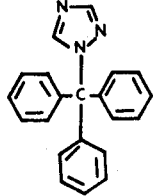

| Active compound | Erysiphe test Infection in % of the infection of the untreated control at an active compound concentration of 0.00025% by weight |
|---|---|
| (known) (B) | 41 |
| (2) | 0 |
| (8) | 10 |
| (9) | 29 |
| (15) | 2 |
| (13) | 2 |

EXAMPLE 7

Erysiphe test / systemic

Solvent: 4.7 parts by weight of acetone
Dispersing agent: 0.3 part by weight of alkylaryl polyglycol ether
Water: 95 parts by weight The amount of active compound required for the desired concentration of the active compound in the watering liquid was mixed with the stated amount of the solvent and the concentrate was diluted with the stated amount of water which contained the stated additions.

Cucumber plants grown in standard soil, in the 1–2 leaf stage, were watered three times within a week with 20 ml of the watering liquid having the stated concentration of active compound, per 100 ml of soil.

After the treatment, the plants treated in this way were inoculated with the conidia of the fungus *Erysiphe cichoracearum*. The plants were then placed in a greenhouse at 23° to 24°C and a relative atmospheric humidity of 70%. After 12 days, the infection of the cucumber plants was determined as a percentage of the untreated but also inoculated control plants.

0% means no infection and 100% means that the infection was exactly as great as in the case of the control plants.

The active compounds, the concentrations of the active compound and the results can be seen from the table which follows:

Table 3

| Active compound | Erysiphe test / systemic Infection in % of the infection of the untreated control at an active compound concentration of | |
|---|---|---|
| | 100 ppm | 1 ppm |

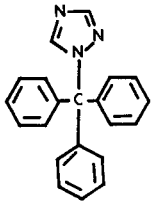

| | 91 | |
| (known) (B) | | |
| (14-threo form) | 0 | |
| (14-erythro form) | 0 | |
| (4) | 0 | |
| (2) | 0 | |

EXAMPLE 8

Podosphaera test (powdery mildew of apples) / Protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (*Podosphaera leucotricha Salm.*) and placed in a greenhouse at a temperature of 21° – 23°C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 4

| Active compound | Podosphaera test / protective Infection in % of the infection of the untreated control at an active compound concentration (in % by weight) of | |
|---|---|---|
| | 0.00062 | 0.00031 |

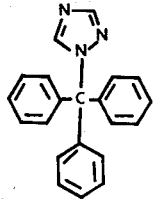

| | 52 | 79 |
| (known) (B) | | |
| (2) | 5 | 16 |
| (14-threo form) | 0 | — |
| (14-erythro form) | 0 | — |
| (4) | 0 | — |
| (15) | 4 | — |

EXAMPLE 9

Shoot treatment test / powdery mildew of cereals / protective (leaf-destructive mycosis)

To prepare a suitable preparation of active compound, 0.25 part by weight of active compound was taken up in 25 parts by weight of dimethylformamide and 0.06 part by weight of emulsifier W, and 975 parts by weight of water were added. The concentrate was diluted with water to the desired final concentration of the spray liquor.

To test the protective activity, young barley plants of the Amsel variety, having one leaf, were sprayed with the preparation of the active compound until dew-moist. After drying, the barley plants were dusted with spores of *Erysiphe graminis var. hordei*.

After 6 days residence time of the plants at a temperature of 21° to 22°C and an atmospheric humidity of 80 to 90% the occurrence of mildew pustules on the plants was evaluated. The degree of infection is expressed as a percentage of the infection of the untreated control plants. 0% denotes no infection and 100% denotes the same degree of infection as in the untreated control. The active compound is regarded as the more active, the lower the infection with powdery mildew.

The active compounds, active-compound concentrations in the spray liquor and degrees of infection can be seen from the table which follows:

Table 5

| Shoot treatment test / powdery mildew of cereals / protective | | |
|---|---|---|
| Active compounds | Active compound concentration in the spray liquor, in % by weight | Infection in % of the untreated control |
| untreated | — | 100 |
| CH$_2$—NH—CS—S\\ \ \ \ \ \ \ \ \ \ \ \ \ \ \ \ \ \ \ \ \ \ \ \ \ \ \ \ Zn CH$_2$—NH—CS—S/ (known) (C) | 0.3 | 64.0 |
| | 0.1 | 80.5 |

Table 6

| | Powdery mildew of barley test (Erysiphe graminis var. hordei) / systemic | | |
|---|---|---|---|
| Active compounds | Active compound concentration in the dressing in % by weight | Amount of dressing used in g/kg of seed | Infection in % of the untreated control |
| without dressing | — | — | 100 |
| 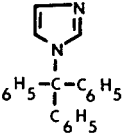 (known) (A) | 30 | 10 | 100 |
| CH₂—NH—CS—S\<br>                  Zn<br>CH₂—NH—CS—S/<br>(known) (C) | 30 | 10 | 100 |
| (2) | 25 | 10 | 0.0 |

Table 5-continued

| | Shoot treatment test / powdery mildew of cereals / protective | |
|---|---|---|
| Active compounds | Active compound concentration in the spray liquor, in % by weight | Infection in % of the untreated control |
| (2) | 0.01 | 0.0 |
| | 0.001 | 0.0 |
| (6) | 0.01 | 6.3 |
| | 0.001 | 10.8 |
| (14-erythro form) | 0.01 | 0.0 |
| | 0.001 | 0.0 |
| (14-threo form) | 0.01 | 0.0 |
| | 0.001 | 0.0 |
| (12) | 0.01 | 0.0 |
| | 0.001 | 0.0 |
| (7) | 0.01 | 0.0 |
| | 0.001 | 23.8 |
| (4) | 0.01 | 0.0 |
| | 0.001 | 0.0 |
| (17) | 0.01 | 0.0 |
| | 0.001 | 6.3 |

EXAMPLE 10

Powdery mildew of barley test (*Erysiphe graminis var. hordei*)/systemic (fungal cereal shoot disease)

The active compounds were applied as pulverulent seed dressings. They were prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flower pots, 2 cm deep in a mixture of one part by volume of Fruhstorfer standard soil and one part by volume of quartz sand. Germination and emergence took place under favorable conditions in a greenhouse. 7 days after sowing, when the barley plants had developed their first leaf, they were dusted with fresh spores of *Erysiphe graminis var. hordei* and grown further at 21° to 22°C and 80 to 90% relative atmospheric humidity and 16 hours' light exposure. The typical powdery mildew pustules formed on the leaves within 6 days.

The degree of infection is expressed as a percentage of the infection of the untreated control plants. Thus, 0% denotes no infection and 100% denotes the same degree of infection as in the case of the untreated control. The activity of a compound is inversely related to the infection with powdery mildew.

The active compounds, active-compound concentrations in the seed dressing, the amount of dressing used, and the percentage infection with powdery mildew can be seen from the table which follows:

EXAMPLE 11

Fuusicladium test (apple scab)/Protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated with an aqueous conidium suspension of the apple scab causative organism (*Fusicladium dendriticum Fuckel*) and incubated for 18 hours in a humidity chamber at 18° – 20°C and at a relative atmospheric humidity of 100%.

The plants were then brought into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 7

| | Fusicladium test / protective | |
|---|---|---|
| Active compound | Infection in % of the infection of the untreated control at an active compound concentration (in % by weight) of | |
| | 0.025 | 0.00125 |
| 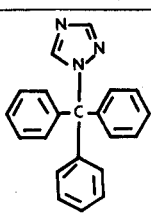 (known) (B) | 97 | — |
| (2) | — | 16 |
| (14-threo form) | — | 7 |
| (14-erythro form) | — | 5 |
| (12) | — | 0 |
| (4) | — | 12 |

It will be appreciated that the instant specification and examples are set forth by way of illustration and not limitation, and that various modifications and changes may be made without departing from the spirit and scope of the present invention.

What is claimed is:

1. A triazolyl-O,N-acetal of the formula

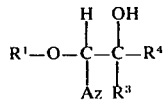

in which
R¹ is phenyl, chlorophenyl, fluorophenyl, bromophenyl, nitrophenyl, diphenyl, chlorodiphenyl, or alkyl-phenyl, alkoxy-phenyl or carbo alkoxyphenyl wherein the alkyl moieties have up to 4 carbon atoms,
R³ is hydrogen, alkyl with up to 4 carbon atoms or benzyl,
R⁴ is alkyl with up to 4 carbon atoms, phenyl, chlorophenyl, cyclopentyl or cyclohexyl,
Az is a 1,2,4-triazolyl-(1), 1,2,4-triazolyl-(4) or 1,2,3-triazolyl-(1) radical.
or a salt thereof with a physiologically tolerated acid.

2. The compound according to claim 1 wherein such compound is 1-(4'-chlorophenoxy)-1-[1,2,4-triazolyl-(1')]-3,3-dimethyl-butan-2-ol of the formula

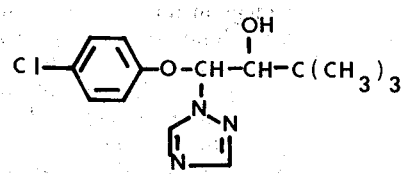

3. The compound according to claim 1 wherein such compound is 1-(4'-chlorophenoxy)-1-[1,2,4-triazolyl-(1')]-2-methyl-3,3-dimethyl-butan-2-ol of the formula

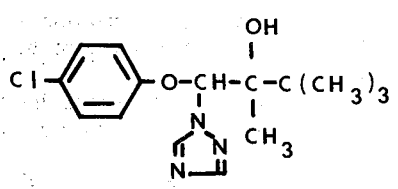

4. The compound according to claim 1 wherein such compound is 1-(4'-bromophenoxy)-1-[1,2,4-triazolyl-(1')]-3,3-dimethyl-butan-2-ol of the formula

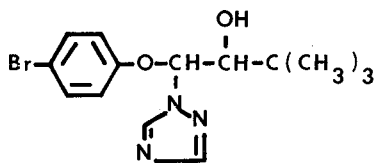

5. The conpound according to claim 1 wherein such compound is 1-(4'-diphenoxy)-1-[1,2,4-triazolyl-(1')]-3,3-dimethyl-butan-2-ol of the formula

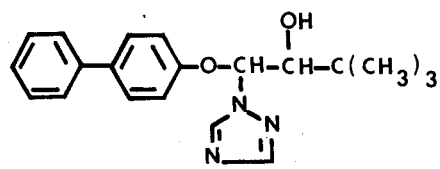

6. The compound according to claim 1 wherein such compound is 1-(2',4'-dichlorophenoxy)-1-[1,2,4-triazolyl-(1')]-3,3-dimethyl-butan-2-ol of the formula

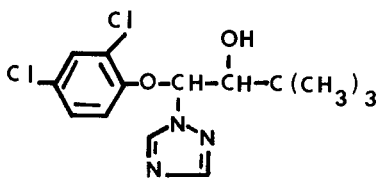

7. The compound according to claim 1 wherein such compound is 1-(4'-fluorophenoxy)-1-[1,2,4-triazolyl-(1')]-3,3-dimethyl-butan-2-ol of the formula

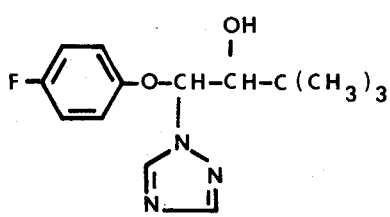

* * * * *

UNITED STATES PATENT AND TRADEMARK OFFICE
CERTIFICATE OF CORRECTION

PATENT NO. : 3,952,002
DATED : April 20, 1976
INVENTOR(S) : Wolfgang Kramer et al It is certified that error appears in the above-identified patent and that said Letters Patent are hereby corrected as shown below:

Column 18, under heading "Az", compound 18, cancel "  "

and substitute therefor: --  --.

Signed and Sealed this

Twenty-fifth Day of September 1979

[SEAL]

Attest:

Attesting Officer

LUTRELLE F. PARKER
*Acting Commissioner of Patents and Trademarks*